United States Patent [19]

Duranleau et al.

[11] 4,341,531

[45] Jul. 27, 1982

[54] PRODUCTION OF METHANE-RICH GAS

[75] Inventors: Roger G. Duranleau, Georgetown, Tex.; Walter C. Gates, Jr., Carmel, N.Y.

[73] Assignee: Texaco Inc., White Plains, N.Y.

[21] Appl. No.: 214,377

[22] Filed: Dec. 8, 1980

[51] Int. Cl.³ .......................... C07C 1/04; C07C 1/10
[52] U.S. Cl. .................................. 48/197 R; 518/703; 518/705; 518/711; 518/715; 252/474
[58] Field of Search ............... 518/703, 705, 711, 715; 48/197 R, 215

[56] References Cited

U.S. PATENT DOCUMENTS

| | | | |
|---|---|---|---|
| 3,709,669 | 1/1973 | Marion et al. | 518/703 |
| 3,890,113 | 6/1975 | Child et al. | 518/703 |
| 3,922,148 | 11/1975 | Child | 518/703 |
| 4,011,058 | 3/1977 | Johnson et al. | 518/703 |
| 4,032,556 | 6/1977 | Banks | 518/715 |
| 4,081,253 | 3/1978 | Marion | 518/703 |

*Primary Examiner*—Howard T. Mars
*Attorney, Agent, or Firm*—Carl G. Ries; Robert A. Kulason; Albert Brent

[57] ABSTRACT

Methane-rich gas is produced by reacting gas mixtures comprising CO and at least one member selected from the group consisting of $H_2$ and $H_2O$, such as synthesis gas, in a reactor containing an improved unsupported catalyst comprising an alkali-metal promoted partially reduced mixture of at least one nickel uranate and at least one oxide of nickel. The weight percent uranium present in the activated catalyst, based on total weight of catalyst composition, is in the range of over 50 to about 90.

29 Claims, 1 Drawing Figure

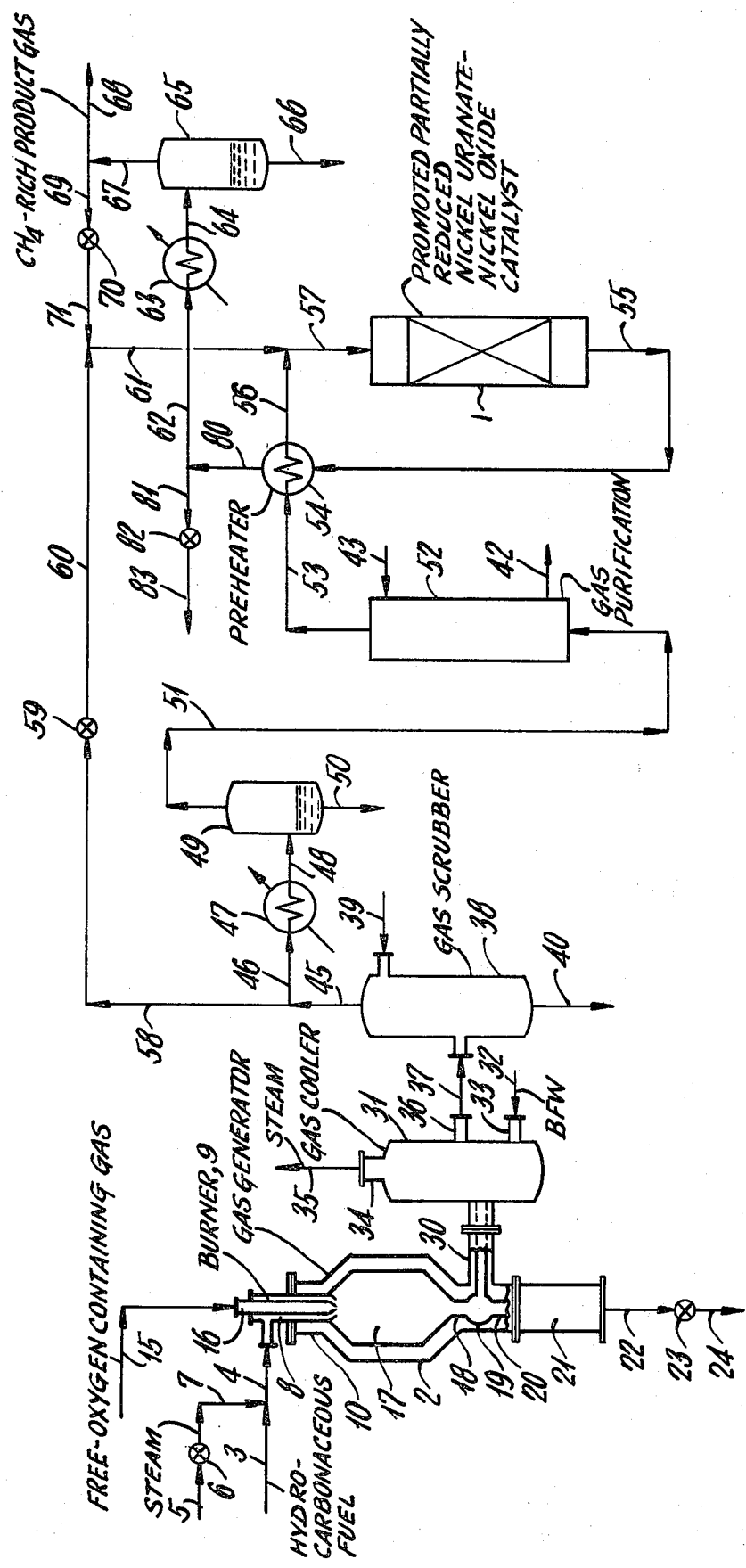

PRODUCTION OF METHANE-RICH GAS

BACKGROUND OF THE INVENTION

1. Field of the Invention

This invention relates to an improved process and catalyst for the production of methane-rich gas. More specifically, the present invention relates to the production of a product gas stream comprising at least 25 vol. % methane (dry basis) by reacting a feed gas stream, such as that produced by the partial oxidation of a liquid hydrocarbonaceous or solid carbonaceous fuel, in a reactor containing the improved catalyst. The product gas may be burned as a fuel without polluting the environment.

2. Description of the Prior Art

Synthesis gas containing methane may be made by the partial oxidation of a hydrocarbonaceous fuel using comparatively high steam to fuel weight ratios and no subsequent catalytic methanation step, as described in coassigned U.S. Pat. No. 3,688,438. In coassigned U.S. Pat. No. 3,890,113, a gaseous stream comprising $H_2O$ and CO is produced by the partial oxidation of a hydrocarbonaceous fuel and is subjected to the water-gas shift reaction to produce a gaseous stream rich in $H_2$ and $CO_2$. This gas mixture is then subjected to conventional catalytic methanation after the mole ratio $H_2/CO_2$ is adjusted to about 4 to 10. In coassigned U.S. Pat. No. 3,888,043, a large amount of nitrogen diluent is contained in the effluent gas stream from the partial oxidation generator. During the two conventional methanation steps with an intervening water-gas shift conversion step, the large amount of nitrogen diluent in the reacting gas stream helps to control the normally vigorous exothermic reactions which are going on.

In U.S. Pat. No. 4,032,556, the methane content of a gas produced by the hydrogenation of a liquid hydrocarbon with a hydrogenating gas at high temperatures is increased by contacting the gas stream with a supported nickel-urania hydrogenation catalyst comprising a maximum of 10 wt. % uranium. U.S. Pat. No. 3,993,459 pertains to a catalyst for converting higher hydrocarbons into gas mixtures containing carbon monoxide, methane and/or hydrogen in which the active components are oxides of the metals lanthanum, cobalt, nickel, uranium, cerium and thorium on an oxide substrate. The catalyst comprises from about 0.1 to 8 percent by weight of uranium. In U.S. Pat. No. 3,847,836 liquid hydrocarbons e.g. naphtha are steam reformed using a catalyst comprising nickel, and/or nickel oxide, together with a relatively smaller amount of uranium oxide supported on a carrier.

SUMMARY

This is a process employing an improved catalyst for producing a methane-rich gas comprising at least 25 vol. % methane (dry basis) from a CO-containing gas mixture. The catalyst is operable over a wide temperature range. The feed gas stream comprises CO and at least one member selected from the group consisting of $H_2$ and $H_2O$ in which the mole ratio of either $H_2/CO$ or $H_2O/CO$ ranges from about 0 to 10.0, such as 0 to 5, and the remaining ratio is in the range of about 0.3 to 10, such as 0.3 to 5. Preferably, the raw feed gas may be obtained from the partial oxidation of liquid hydrocarbonaceous or solid carbonaceous fuels. In such case in addition to CO and $H_2$ and/or $H_2O$, the feed gas may also comprise at least one member selected from the group consisting of $CO_2$, $CH_4$, $N_2$ and Ar. The high activity of the subject catalyst permits removal of trace amounts of CO from a gas mixture.

The feed gas is reacted in a fixed bed reactor containing an improved unsupported catalyst consisting essentially of an alkali-metal promoted partially reduced mixture of at least one nickel uranate and at least one oxide of nickel. The weight percent uranium present in the activated catalyst, based on the total weight of the catalyst composition, is in the range of over 50 to about 90, such as about 60-80; and the weight ratio U/Ni is in the range of about 7-1, such as about 5-2, say 3. Preferably, the uranium in the catalyst composition comprises at least 99.7 wt. % $^{238}U$ isotope. The catalyst has a low reaction initiation temperature, i.e. about 375° F. and is highly active up to about 1500° F. Water-gas shift and methanation reactions may take place simultaneously in the reactor. While the dry methane-rich product gas comprises at least 25 vol. % methane, it may range up to about 97 vol. % methane on a single pass basis.

BRIEF DESCRIPTION OF THE DRAWING

The invention will be better understood by reference to the drawing, which illustrates one embodiment of the disclosed process.

DESCRIPTION OF THE INVENTION

The present invention pertains to an improved continuous process for the production of a gaseous stream comprising 25 to about 97 vol. % $CH_4$ (dry basis) or more by the catalytic reaction of CO and at least one member of the group consisting of $H_2$ and $H_2O$. An improved, unsupported catalyst consisting essentially of an alkali-metal promoted, partially reduced mixture of at least one nickel uranate and at least one oxide of nickel is employed as the catalyst in the subject process.

A particular advantage of the subject process is that the gaseous feedstock may be produced from readily available, comparatively low cost, hydrocarbonaceous and carbonaceous materials e.g., liquid and solid fuels which may contain a comparatively high content of ash and sulfur. When necessary, the feed gas is purified prior to being introduced into the catalytic reactor. The product gas has a heating value in the range of about 400 to 1000 British Thermal Units per standard cubic foot (dry, $CO_2$-free basis), depending upon the methane content. The product gas may be used as a substitute for natural gas or in organic chemical synthesis when the methane content is greater than 95 mole %.

The feed gas being catalytically reacted in the subject process may vary in composition from mixtures of pure CO and $H_2O$ to mixtures comprising a trace of CO in an $H_2$ stream. Thus, the feed gas stream for producing a $CH_4$-rich gas comprises carbon monoxide and at least one member selected from the group consisting of $H_2$ and $H_2O$ in which the mole ratio of either $H_2/CO$ or $H_2O/CO$ ranges from about 0 to 10.0, such as 0 1 to 5, and the remaining ratio is in the range of about 0.3 to 10, such as 0.3 to 5.

The feed gas may be produced by the partial oxidation of a hydrocarbonaceous or carbonaceous fuel followed by gas purification. In such case in addition to CO and $H_2$ and/or $H_2O$, the feed gas stream may also contain at least one member selected from the group consisting of $CO_2$, $CH_4$, $N_2$ and Ar. It was unexpectedly found that carbon may be prevented from depositing on the catalyst in the reactor by maintaining the feed gas stream with a minimum atomic ratio H/C of 2. The source of the hydrogen may be $H_2$ or $H_2O$.

Any conventional source of CO in admixture with $H_2$ and/or $H_2O$ may be employed for the feed stream to the catalytic reactor. For example, catalytic steam reforming and particularly the partial oxidation process are suitable. The partial oxidation of a hydrocarbonaceous fuel i.e. liquid hydrocarbons or solid carbonaceous fuel such as coal with a free-oxygen containing gas with or without a temperature moderator produces mixtures of $H_2$ and CO in which the mole ratio $H_2/CO$ may vary in the range of about 0.30 to 5 depending on the source of carbon used. While the above customary convention has been adopted herein for expressing ranges of ratios, the aforesaid range of ratios may also be expressed in the following manner: 0.30/1 to 5/1. In general, western coals and lignites will yield gas mixtures in which the mole ratio $H_2/CO$ may vary in the range of about 0.4 to 0.6. In another embodiment, the high activity of the subject catalyst permits the removal of trace amounts i.e. up to 2 mole % of CO from the gas mixture.

Conventional methods of making synthetic natural gas (SNG) require a mole ratio $H_2/CO$ in the range of about 1 to 3 as shown by the following equations:

$$CO + 3H_2 \rightarrow CH_4 + H_2O \quad (1)$$

$$2CO + 2H_2 \rightarrow CH_4 + CO_2 \quad (2)$$

In order to realize such a ratio, in many prior art processes a portion of the gasification product containing CO is first catalytically reacted with $H_2O$ in a separate reactor over a separate water-gas shift catalyst to produce $H_2$ and $CO_2$. The $CO_2$ is then removed, and the $H_2$ is added to the original stream to produce the desired ratio of $H_2/CO$. The gas mixture is then reacted over a separate methanation catalyst in a separate reactor to produce $CH_4$.

In contrast, it has been found that the subject improved catalyst unexpectedly acts simultaneously as a water-gas shift catalyst and as a methanation catalyst. Advantageously by this means, only a single bed of the subject catalyst is required. This permits significant savings in the cost of catalyst and equipment. Further, wasteful intermediate gas cooling and purification steps may be eliminated. Process control is less critical as the mole ratios $H_2/CO$ and/or $H_2O/CO$ in the feed gas may vary over a wide range.

A wide variety of hydrocarbonaceous fuels is suitable as feedstock for the partial oxidation process, either alone or in combination with each other or with particulate carbon. The hydrocarbonaceous feeds include by definition fossil fuels such as various liquid hydrocarbon fuels including petroleum distillates and residua, naphtha, asphalt, gas oil, residual fuel, reduced crude, fuel oil, whole crude, coal tar, coal derived oil, shale oil, tar sand oil and mixtures thereof. Suitable liquid hydrocarbon fuel feeds as used herein are by definition liquid hydrocarbonaceous fuel feeds that have a gravity in degrees API in the range of about −20 to 100.

Pumpable slurries of solid carbonaceous fuels, e.g., lignite, bituminous and anthracite coals, coal char, particulate carbon, petroleum coke, and mixtures thereof in water or in said liquid hydrocarbon fuels are included herewith as within the scope of the definition for hydrocarbonaceous fuel feeds.

Further, included also by definition as a hydrocarbonaceous fuel are liquid oxygenated hydrocarbonaceous materials i.e., liquid hydrocarbon materials containing combined oxygen, including alcohols, ketones, aldehydes, organic acids, esters, ethers, and mixtures thereof. Further, a liquid oxygenated hydrocarbonaceous material may be in admixture with one of said liquid petroleum materials.

The term free-oxygen containing gas or gaseous oxidant as used herein is intended to mean a gas selected from the group consisting of air, oxygen-enriched air (22 mole percent $O_2$ and higher), and preferably substantially pure oxygen (95 mole percent $O_2$ and higher). The amount of nitrogen in the product gas may be substantially reduced or eliminated by using substantially pure oxygen. The ratio of free-oxygen in the gaseous oxidant to carbon in the feedstock (O/C, atom/atom) is in the range of about 0.6 to 1.5, suitably about 0.7 to 1.2 and preferably below 1.0.

$H_2O$ is preferably introduced into the reaction zone to help control the reaction temperature, to act as a dispersant of the hydrocarbonaceous fuel fed to the reaction zone, and to serve as a reactant to increase the relative amount of hydrogen produced. About 0.15 to 5.0 pounds of $H_2O$ are introduced per pound of hydrocarbonaceous fuel. Other suitable temperature moderators include $CO_2$-rich gas, a cooled portion of effluent gas from the gas generator, cooled off-gas from an integrated ore-reduction zone, nitrogen, and mixtures thereof.

The subject improved catalyst comprises an alkali-metal promoted partially reduced mixture of at least one nickel uranate selected from the group consisting of $NiUO_4$ and $NiU_3O_{10}$, and at least one oxide of nickel selected from the group consisting of $NiO$ and $Ni_3O_4$. The total amount of uranium present in the partially reduced catalyst, based on the total weight of the partially reduced i.e. activated catalyst composition, is in the range of over 50 to about 90, say about 60 to 80 weight percent. The weight ratio U/Ni of the activated catalyst is in the range of about 7-1, such as 5-2, say 3.0.

Preferably, the uranium in the present catalyst composition comprises at least 99.7 weight percent $^{238}U$ isotope. Advantageously, the tailings produced by conventional $^{235}U$ enrichment processes may be easily converted into $U_3O_8$ in which at least 99.7 wt. % of the uranium is present as $^{238}U$ isotope. Thus, tailings which were once a burdensome waste material may now be used as a low cost raw material for the production of the catalyst of the subject invention.

The expression "alkali-metal" promoter includes at least one member selected from the group consisting of potassium, sodium, and cesium. Typical examples of alkali metal compounds that may be used in the production of the subject catalyst composition to supply said alkali metals are the respective alkali metal oxides or the salts of oxygen-containing acids such as carbonates, bicarbonates, nitrates, oxalates and acetates, and/or hydroxides of said alkali metals which yield the oxides at elevated temperatures. The preferred alkali metal in the activated catalyst is potassium in the form of the compound $K_2O$. The alkali metal compound content of the catalyst may range from about 0.01 to 2 weight percent, say about 0.5-1 weight percent based on the total weight of the catalyst.

Most conventional catalysts employ a suitable support material such as aluminum oxide, silicon oxide, or an oxide of magnesium, calcium, or barium. In contrast, the subject improved bulk catalyst is unsupported. A completely inactive catalyst resulted when the ingredients of the subject catalyst were incorporated on said supporting materials.

The subject catalysts are prepared, primarily, by thermally decomposing nickel nitrate hexahydrate and an alkali metal compound in the presence of at least one oxide of uranium selected from the group consisting of $U_3O_8$, $UO_3$, and $UO_2$. A mixture consisting essentially of at least one nickel oxide, and at least one nickel uranate, and an alkali metal oxide is thereby produced, such as the following mixtures of compounds in weight percent:

Formula A—NiO 1.0 to 30, $Ni_3O_4$ trace to 30, $NiUO_4$ 70 to 98, and $K_2O$ 0.01 to 2.0.

Formula B—NiO 1.0 to 30, $NiU_3O_{10}$ 70 to 98, and $K_2O$ 0.01 to 2.0.

Formula C—NiO 1.0 to 30, $NiUO_4$ 30 to 68, $NiU_3O_{10}$ 30 to 68, and $K_2O$ 0.01 to 2.0.

It is necessary to partially reduce the aforesaid mixtures by treatment with pure hydrogen at high temperatures and pressures in order to produce the activated catalyst of the subject invention. After said treatment with hydrogen, at least 30 up to about 80, say 40 to 60 wt. % of the nickel present in the activated catalyst is in the metallic state. From about 85 to 100, such as at least 90 wt. % of the remainder of the nickel present in the activated catalyst may be in the form of at least one nickel uranate selected from the group consisting of $NiUO_4$ and $NiU_3O_{10}$. The balance of nickel, if any, may be present in the activated catalyst in the form of at least one oxide of nickel selected from the group consisting of NiO and $Ni_3O_4$. From about 10 to 100, such as about 20 to 80, say at least 90 wt. % of the uranium in the activated catalyst may be present in the form of at least one nickel uranate selected from the group consisting of $NiUO_4$ and $NiU_3O_{10}$. The balance of uranium, if any, may be present in the activated catalyst in the form of at least one oxide of uranium selected from the group consisting of $U_3O_8$, $UO_3$ and $UO_2$.

In the preparation of the subject catalyst, about 29.1 g to 2,910 g such as 0.1 to 10 moles of nickel nitrate hexahydrate ($Ni(NO_3)_2 \cdot 6H_2O$) are heated in a stainless steel vessel to a temperature in the range of about 130° to 200° F., such as 134° to 150° F. and melted. The material is stirred as it is heated and 0.05 to 18.0 g, such as 0.0036 to 0.1333 moles of an alkali metal compound having the formula M-A wherein M is an alkali metal selected from the group consisting of Na, Ce, and K, and A is a member selected from the group consisting of $CO_3$, $HCO_3$, $NO_3$, OH, oxalate and acetate, are added to the melt. The mixture is continually stirred at the melting temperature and 84 g to 8420 g, such as 0.1 to 10 moles, of at least one uranium oxide selected from the group consisting of $U_3O_8$, $UO_3$, and $UO_2$ are gradually added over a period of about 15 to 25 minutes.

After emission of nitrogen oxides and frothing ceases, the product thickens to a brown mass having a rubbery consistency. Mixing is continued from about 20 to 100 minutes. The mass is then cut up into small chunks and then heated for 16 to 24 hours at a temperature in the range of about 50° to 200° F. The chunks are then dried for 1 hour in a forced air oven at a temperature in the range of about 160° to 350° F., and then heated in a muffle furnace to a temperature of about 400° F. The temperature is raised 100° F. per hour until a temperature in the range of about 675° to 725° F. is reached and maintained for about 2.5 to 3.5 hours.

At this time the material is in the form of a powder whose particle size may be further reduced, by crushing, to about 100 to 1000 microns, such as 150 to 600 microns, say 300 microns. Alternately, the powder may be mixed with a binder, such as stearic acid and molded into pellets having a diameter in the range of about 1/16" to ¼", say 5/32". The pellets are heated in a muffle furnace under a slow stream of nitrogen to a temperature in the range of about 550°-650° F. for 2-3 hours, and then at 750°-850° F. for an additional 3-4 hours.

The catalyst is activated by being partially reduced with pure hydrogen. 1500 to 6500 standard cubic centimeters per minute of $H_2$ per 100 cc of catalyst are passed through the catalyst in a reactor for 10-15 hours at a temperature in the range of about 850°-900° F. and 200-250 psig pressure. The pressure is then increased to about 310 to 350 psig and the hydrogen treatment is continued for an additional 6-8 hours at the same conditions of flow rate and temperature.

Conventional fixed bed, ebullient bed, or fluidized bed reactors may be used for converting the feed gas into the methane-rich gas stream. Preferably, a fixed bed reactor is employed. Since the reaction is highly exothermic, temperature control may be effected by any of the following techniques: distribution of the feed gas throughout the fixed bed reactor by means of separate inlet points, imbedding tubular coolers in the catalyst beds and producing steam which may be used elsewhere in the process, or cooling the effluent gas between beds, with simultaneous steam generation.

Advantageously, no recycle is required with the subject highly active catalyst. However, optionally about 1-25, say about 2-5, volumes of the product gas may be mixed with each volume of fresh feed gas. The temperature of the inlet feed gas stream to the reactor may be in the range of about 375°-725° F., such as about 395°-600° F. The catalyst bed temperatures are not critical and can be allowed to rise as much as 775° F. and still produce near theoretical yields of $CH_4$. The catalyst is active at the lower range and will start to make $CH_4$ and $CO_2$. The bed temperature can climb rapidly to about 1500° F. and still produce near theoretical amounts of $CH_4$.

Space velocities (standard volumes of dry gas per volume of catalyst per hour-vol./vol./hr) may be in the range of about 350-10,000, such as 800-6000. The pressure in the reactor is in the range of about 1-300 atmospheres, such as about 10-150 atmospheres. The reaction time is in the range of about 1-100, such as 3-60 seconds. The catalyst has a long life without appreciable deterioration. Carbon deposition may be resisted by maintaining an atomic ratio in the feed gas of H/C of at least 2. The feed gas stream to the reactor may be preheated to the proper inlet temperature by indirect heat exchange with at least a portion of the effluent gas stream leaving the reactor at a temperature for example in the range of 600° to 1500° F. If necessary, the catalyst may be regenerated and most of its activity restored by hydrogen treatment.

With feedstreams comprising CO in admixture with $H_2$ and/or $H_2O$, the $CH_4$-rich gas stream leaving the catalytic reactor comprises on the dry basis at least 25 mole % to 97 or more mole % $CH_4$. Such clean gas energy has a heating value of about 400 to 1000 BTU/SCF. Using conventional methods the effluent gas from the reactor may be optionally dried and purified by removing unwanted gaseous materials i.e. $CO_2$, $H_2S$, COS, and $N_2$.

DESCRIPTION OF THE DRAWING

In one embodiment of the previously described process, as shown in the accompanying schematic drawing, the feed gas to the CO catalytic reactor 1 is originally produced in the reaction zone of free-flow unpacked noncatalytic partial oxidation synthesis generator 2 at an autogenous temperature in the range of about 1700° to 3000° F. and a pressure in the range of about 1 to 300 atmospheres. Note that, advantageously, there is no separate water-gas shift conversion step in the subject process.

A hydrocarbonaceous feed in line 3 is passed through line 4 with or without a temperature moderator from line 5, valve 6, line 7 and then down through annular passage 8 of burner 9 located in upper central inlet 10 of vertical free-flow refractory lined noncatalytic gas generator 2. Simultaneously, a stream of free-oxygen containing gas in line 15 is passed down through central conduit 16 of burner 9.

Preheating of the reactants is optional but generally desirable. For example, a hydrocarbon oil and steam may be preheated to a temperature in the range of about 100° to 800° F. and the oxygen may be preheated to a temperature in the range of about 100° to 1000° F.

The downflowing feedstreams impinge and the partial oxidation reaction takes place in reaction zone 17. The raw effluent gas stream leaving the partial oxidation gas generator through bottom outlet 18 passes through insulated unit 30 and may have the following composition in mole %: $H_2$ 20–70; CO 15–60; $CO_2$ 3–30; $H_2O$ 5–15; $CH_4$ nil–20; $N_2$ nil–60; $H_2S$ 0–5.0; COS 0–0.2; and Ar 0–2.0.

Unreacted particulate carbon (on the basis of carbon in the feed by weight) entrained in the effluent gas stream comprises about 0.2 to 20 weight percent from liquid feeds but is usually negligible from gaseous hydrocarbon feeds. At least a portion of any entrained particulate solid matter or molten or carbonaceous slag in the hydrocarbonaceous or carbonaceous fuel may be separated from the effluent gas stream leaving the gas generator in a suitable gas-solids separating zone without lowering the temperature or pressure of the gas stream. For example, particulate matter and slag, if any, may separate out in gas diversion and solids separation chamber 19 and pass through passage 20 into slag chamber 21. Slag chamber 21 may be connected in axial alignment with the free-flow gas generator 2. By this means, ash and other solids or molten slag in the gas stream discharging from the lower part of reaction chamber may drop directly into a pool of water contained in the bottom of the slag chamber. The separated material may be periodically removed through line 22, valve 23, and line 24.

The hot effluent gas stream leaving gas diversion and solids separation chamber 19 is passed through insulated line 30 and into gas cooler 31 where it may be cooled to a temperature in the range of about 400° to 800° F., say about 450° to 650° F. by indirect heat exchange with water. Boiler feed water enters gas cooler 31 by way of line 32 and inlet 33. The water is converted into steam which leaves by way of outlet 34 and line 35. By-product steam is thereby produced for use elsewhere in the system and/or for export. Alternatively, all of the hot raw effluent gas steam leaving the gas generator may be cooled by direct quenching in water.

The partially cooled stream of effluent gas leaving gas cooler 31 through outlet 36 and line 37, or the effluent gas stream leaving a quench tank not shown, is passed into a gas cleaning zone where any remaining entrained solids may be removed. Any conventional procedure for removing suspended solids from the gas stream may be employed. For example, the effluent gas stream may be passed through a scrubbing column in direct contact and counterflow with a scrubbing fluid selected from the group consisting of liquid hydrocarbon, dilute mixtures of particulates carbon and scrubbing fluid, or water. A slurry of particulate carbon and scrubbing fluid may be then removed from the bottom of the column and sent to a carbon separation or concentration zone. Carbon concentration may be effected by any suitable conventional means e.g. filtration, centrifuge, gravity settling, or by liquid hydrocarbon extraction such as the process described in coassigned U.S. Pat. No. 4,205,963. In the scheme shown in the drawing, the effluent gas stream is scrubbed with water in gas scrubber 38. The water enters through line 39 and the dispersion of solids and water leaves through line 40 and is sent to a conventional facility not shown for the recovery of water and carbon. The gas stream in line 45 may be then passed directly through lines 58–61 and 57 into catalytic reactor 1. Optionally, recycle gas from line 71 may be mixed with the cooled and cleaned gas stream from line 60.

When necessary, at least a portion of the cooled and cleaned gas stream in line 54 may be treated to remove gaseous impurities i.e. acid-gas. The purified and any unpurified portions of the gas stream are then combined in line 57 and fed to the reactor. In said embodiment, at least a portion i.e. 50–100 volume percent of the clean gas stream leaving gas scrubbers 38 at a temperature in the range of about 375°–725° F. is passed through lines 45, 46 and cooled below the dew point in gas cooler 47. Water and normally liquid hydrocarbons, if any, may be thereby condensed out. The mixture of gas and liquids is passed through line 48 and separated in gas-liquids separator 49. The liquids are removed from separator 49 by way of line 50 at the bottom. The substantially dry gas stream passes overhead through line 51 into the gas purification section 52 at a temperature in the range of about 100°–175° F. Any suitable conventional process may be used for purifying the process gas stream in gas purification section 52. Typical gas purification processes may involve refrigeration and physical or chemical absorption with a solvent, such as methanol, n-methyl-pyrrolidone, triethanolamine, propylene carbonate or alternatively with hot potassium carbonate. For example, the gas stream may be washed with cold methanol and the total sulfur, $H_2S$ plus COS, may be reduced to less than 0.1 ppm. All of the $CO_2$ may be then removed to produce a purified process gas stream containing less than 5 ppm $CO_2$. The solvent is regenerated and recycled to the absorption column for reuse. Thus, rich solvent absorbent is removed from gas purification section 52 by way of line 42, regenerated, and returned as lean solvent absorbent by way of line 43. One or more of the gases separated from the solvent absorbent during regeneration, and preferably $CO_2$, may be recycled to the partial oxidation gas generator as at least a portion of the temperature moderator. When necessary, final clean-up may be accomplished by passing the process gas stream through iron oxide, zinc oxide, or activated carbon to remove residual traces of $H_2S$ or organic sulfide. Thus, at least one of the following gaseous impurities when present in the process gas stream may be removed in gas purification section 52: $CO_2$, $H_2S$, COS, Ar, N₂, and H₂O. Optionally, a portion of the $CO_2$ and/or $N_2$ may be allowed to remain in the process gas stream to impart improved temperature control within catalytic reactor 1. Optionally, at least a portion of the $H_2O$ may be left in the process gas stream for the water-gas shift reaction.

A cleaned and purified gas stream leaves gas purification section 52 through line 53 at a temperature in the range of about 70°–150° F. This gas stream is heated in heat exchanger 54 by indirect heat exchange with the hot product gas leaving reactor 1 by way of line 55 at a temperature in the range of about 600°–1500° F. The heated gas stream leaving heat exchanger 54 passes through lines 56, 57 and enters catalytic reactor 1 at a temperature in the range of about 375°–725° F. The remaining portion, if any, of the cleaned gas stream leaving overheat in line 45 of gas scrubber 38 and by-passing the gas drying and purification sections by way of line 58, valve 59, and lines 60 and 61 is mixed in line 57 with the preheated cleaned, dried, and purified gas stream from line 56. All or a portion of the partially cooled product gas stream leaving heat exchanger 54 by way of line 80 is passed through line 62 and cooled below the dew point in gas cooler 63. Water and any traces of normally liquid hydrocarbons condense out. The mixed phase mixture passes through line 64 into gas-liquids separator 65 where separation takes place. Liquids are removed intermittently from separator 65 by way of line 66 at the bottom. The methane-rich product gas leaves overhead from separator 65 by way of lines 67 and 68. A recycled stream, if any, is passed through line 69, valve 70, lines 71, 61, and mixed in line 57 with the cleaned dried and purified gas stream from line 56. That portion of the partially cooled gas stream from line 80, if any, which is not dewatered, is passed through line 81, valve 82, and line 83.

In one embodiment, the feed gas stream in line 57 contains $H_2O$. $H_2O$ may be added separately in the form of water or steam or alternatively, at least a portion of the $H_2O$ in the gas stream leaving gas scrubber 38 may be allowed to remain. The mole of either $H_2/CO$ or $H_2O/CO$ in the feed gas mixture in line 57 is in the range of 0 to 10, say 0 to 5, and the remaining ratio is in the range of about 0.3 to 10, say 0.3 to 5. Reactor 1 is a fixed bed reactor containing the subject unsupported catalyst comprising a alkali-metal promoted partially reduced mixture of at least one nickel uranate and at least one oxide of nickel. The pressure in reactor 1 is substantially the same as that in partial oxidation gas generator 2 i.e. 1–300 atmospheres, say 10–200 atmospheres, less the ordinary pressure drop in the lines.

The dry product gas in line 68 may have the following composition in mole %: $CH_4$ 25–98, $CO_2$ 1–75, $H_2$ nil-40, CO nil-10, $N_2$ nil-60, and Ar nil-2.0. Any or all of the gaseous impurities may be removed by conventional gas purification methods not shown to produce clean fuel gas or methane. For example, $CO_2$ may be separated and at least a portion recycled to synthesis gas generator 2 as at least a portion of the temperature moderator.

EXAMPLES

The following examples are offered as a better understanding of the present invention, but the invention is not to be construed as limited thereto.

EXAMPLE I

Example I will illustrate a preferred method for preparing a catalyst composition which is activated in Example II according to this invention.

491 gms (1.69 moles) of nickel nitrate hexahydrate $(Ni(NO_3)_2.6H_2O)$ were melted and mixed with 2.0 gms (0.0143 moles) of potassium carbonate ($K_2CO_3$). The mixture was maintained at the melting temperature and continuously stirred while 350 gms (0.417 moles) of triuranium octoxide powder ($U_3O_8$) were added gradually over a twenty minute period. The product thickened to a brown mass having a rubbery consistency. The mass was cut into small chunks and allowed to remain on a steam plate for about 20 hours. After being dried for 1 hour in a forced air oven at a temperature of about 250° F., the chunks were heated in a muffle furnace to a temperature of 400° F. The temperature was then raised 100° F. per hour until 700° F. was reached and then maintained for 3 hours. By that time the chunks had become a fine powder. The powder was further crushed to allow total passage through a 50 mesh screen (297 microns). The powder was then mixed with 10 grams of stearic acid powder and pelleted into 5/32 inch diameter pellets. The pellets were heated in a muffle furnace under a slow stream of $N_2$ for 2 hours, and then for an additional 3 hours at a temperature of 800° F. The final catalyst was designated Catalyst A, and had the following approximate chemical composition in weight percent: NiO 6.5, $Ni_3O_4$ trace, $NiUO_4$ 93.1, and $K_2O$ 0.35. Catalyst A was activated in the manner described in Example II, prior to being used in Examples II to IV. In one embodiment, the uranium in the subject catalyst composition comprised at least 99.7 weight percent $^{238}U$ isotope.

EXAMPLE II

Catalyst A, prepared in accordance with Example I, was used in the production of methane-rich gas after being activated by being partially reduced in the following manner. Catalyst A was inserted in a fixed bed pilot plant reactor simulating the conditions of an adiabatic reactor of industrial size operated without recycle. The reactor was constructed from 54 inches of 1 inch, Sch. 80 316 stainless steel (SS) pipe and had 316 SS seal-pieces at each bed against 4 inch diameter heads. The top seal-piece was provided with a central inlet whereas the bottom seal-piece had a side outlet. The reaction chamber nominally contained 100 cc of Catalyst A in a 10-inch bed.

Catalyst A was treated within the reactor with 2,000 standard cubic centimeters per minute of pure hydrogen for a period of 10 hours at a temperature of 850° F. and a pressure of 200 psig. This was followed by an additional 6 hours of treatment with hydrogen at the same flow and temperature conditions but at a pressure of 320 psig. By means of the previously described treatment with hydrogen, Catalyst A was partially reduced so that about 50–60 weight percent of the nickel was present in the metallic state. The uranium was present in the activated catalyst primarily in the form of $NiUO_4$ and less than 5 weight percent of at least one oxide of uranium selected from the group consisting of $UO_3$ and $UO_2$. The weight percent of uranium present in the activated catalyst, based on the total weight of the activated catalyst, was 64.2. The weight ratio U/Ni in the activated catalyst was about 3.0.

Runs 1 to 6 in Table I below, illustrate the use of the activated catalyst of the subject invention as prepared in Examples I and II. Data is provided in Table I for the production of methane-rich gas comprising at least 26 mole percent (dry basis) of $CH_4$ by passing a feed gas comprising CO and at least one member of the group consisting of $H_2$ and $H_2O$ through a fixed-bed reactor containing the subject catalyst. Means were employed in the process for cooling the off gas from the reactor to below the dew point of a normally liquid materials in the off gas, and collecting and separating the liquids from the gas stream. Conventional equipment for measuring and controlling the rate of flow of the feed and product streams, temperature and pressure, and sampling and metering were provided.

The methane content of the product gas, and accordingly the heating value, was maximized i.e. 53.3-97.4 mole percent $CH_4$ in Runs 1-3 by introducing a dry feed gas into the reaction zone. Further, in Runs 1-3 there were about 100% conversions of CO and $H_2$. While the mole ratio $H_2/CO$ was greater in Run 1 than in Run 3, the reaction conditions were milder and the methane content of the product gas was higher in Run 1 in comparison with Run 3. Run 1 clearly shows the high activity of the subject catalyst at low temperatures i.e. 395° F. by converting 100% of the CO and $H_2$ in the feed gas into a product gas containing 97.4 mole percent methane. A large amount of $CO_2$ was produced in the product gas in Run 2 by reducing the mole ratio $H_2/CO$ of the feed gas to the catalytic reactor to about 1.

Run 4 shows that the subject catalyst has the property of catalyzing the water-gas shift reaction. The feed gas in Run 4 comprises CO and $H_2O$, but no hydrogen. The mole ratio $H_2O/CO$ was 1. Substantially all of the CO was converted in the reactor. First, by the water-gas shift reaction, a portion of the CO in the feed gas was reacted with $H_2O$ to produce $H_2$ and $CO_2$. Then, the $H_2$ was reacted with the remainder of the CO to produce $CH_4$ and $CO_2$. In Run 5, the feed gas contained $H_2$, CO, and $H_2O$. The increased amount of $H_2$ in the feed resulted in an increased yield of $CH_4$ in Run 5 in comparison with that produced in Run 4.

EXAMPLE III

Runs 5, 6, and 7 illustrate the thermal stability of the activated catalyst prepared according to this invention in comparison with a commercial nickel catalyst. In Runs 5 and 6, the average bed temperatures for the subject catalyst ranged from about 904° to 1061° F., while maximum bed temperatures may range up to about 1350° to 1500° F. CO and $H_2$ conversions were high i.e. 64 to 100 percent; and, the dry product gas contained from about 33 to 50 mole percent $CH_4$. For comparison, Run 7 and made using a commercial nickel methanation catalyst 104. However, in Run 7 rapid deactivation of the commercial nickel catalyst took place when the average temperature of the bed reached above 990° F. The percent conversion of CO and $H_2$ fell rapidly to respectively 16 and 24.8. The mole percent methane in the dry product gas was only about 7.

EXAMPLE IV

The high percent conversion of CO and $H_2$ and the high yield of $CH_4$, as in Runs 1-3, illustrate the high activity of the catalyst of the subject invention in comparison with the typical commercial iron oxide Fischer Tropsch catalyst that was employed in Run 8. Further, carbon containing liquids were produced in Run 8, while none were produced in Runs 1-3. These differences clearly distinguish between the two catalysts. The catalysts of the subject invention produce mainly $CH_4$ at conditions where normal Fischer Tropsch catalysts produce multicarbon compounds. The comparatively high level of CO conversion at low $H_2/CO$ ratios also points out the ability of the catalysts of the subject invention to catalyze the water-gas shift reaction simultaneously with the methanation reaction.

The overall results as shown in Table I serve to point out that the activated catalyst of the subject invention is very active, has good selectivity to methane, and has good thermal resistance.

TABLE I

| Run No. | Feed Gas Mole Ratio | | Reaction Conditions | | | | % Conversion | | Product Gas Mole % (dry Basis) | | Carbon Containing Liquids | Catalyst |
| --- | --- | --- | --- | --- | --- | --- | --- | --- | --- | --- | --- | --- |
| | $H_2/CO$ | $H_2O/CO$ | Pressure Atm. | Temp. °F. | SV vol/vol/hr | Time Sec. | CO | $H_2$ | $CO_2$ | $CH_4$ | % | |
| 1 | 3.13 | 0 | 100 | 395 | 2494 | 6.5 | 100 | 100 | 2.6 | 97.4 | 0 | (a) |
| 2 | 1.06 | 0 | 100 | 709 | 1226 | 9.6 | 100 | 100 | 46.7 | 53.3 | 0 | (a) |
| 3 | 1.70 | 0 | 300 | 583 | 1633 | 22.3 | 100 | 99.6 | 5.2 | 93.0 | 0 | (a) |
| 4 | 0 | 1 | 300 | 877 | 2477 | 6 | 99.9 | — | 73.4 | 26.0 | 0 | (a) |
| 5 | 1.00 | 0.80 | 300 | 1061 | 4917 | 3.7 | 99.7 | 100 | 49.6 | 50.4 | 0 | (a) |
| 6 | 3.19 | 0 | 300 | 904.6 | 7602 | 3.7 | 100 | 64 | 11.1 | 33 | 0 | (a) |
| 7 | 2.24 | 0 | 300 | 900 | 4561 | 6.3 | 16 | 24.8 | 1.1 | 7.0 | 0 | (b) |
| 8 | 1.85 | 0 | 300 | 490 | 582 | 68.6 | 43.7 | 25.5 | — | 6.3 | 6.2 | (c) |

(a) Catalyst A prepared in Example I and activated in Example II.
(b) Commercial nickel methanation catalyst 104.
(c) Commercial iron oxide Fischer Tropsch catalyst.

It will be evident to those skilled in the art that various modifications of this invention can be made, or followed, in the light of the foregoing disclosure and discussion, without departing from the spirit or scope thereof.

We claim:

1. A process for the production of a methane-containing gas comprising:
   (1) introducing a gas mixture comprising CO and at least one member of the group consisting of $H_2$ and $H_2O$ at a temperature in the range of about 375° to 1500° F. and a pressure in the range of about 1 to 300 atmospheres into a reaction zone containing an unsupported catalyst comprising an alkali-metal promoted partially reduced mixture of at least one nickel uranate and at least one oxide of nickel, wherein the total weight percent of uranium present in said catalyst basis total weight of said catalyst composition is in the range of over 50 to about 90 weight percent;
   (2) converting CO in said gas mixture into $CH_4$ by reacting CO in said reaction zone with hydrogen which is either (a) introduced with said gas mixture, (b) produced by the water-gas shift reaction in said reaction zone, or both (a) and (b); and (3) removing a $CH_4$-containing gas from said reaction zone.

2. The process of claim 1 wherein the mole ratio of either $H_2/CO$ or $H_2O/CO$ in the feed gas mixture reacted in (2) is in the range of 0 to about 10 and the other mole ratio is in the range of about 0.3 to 10.

3. The process of claim 1 wherein the minimum atomic ratio H/C of the gas mixture reacted in (2) is 2.

4. The process of claim 1 provided with the steps of cooling the $CH_4$-containing gas stream from (2) below the dew point, and separating water to produce a dry gas stream comprising at least 25 mole % $CH_4$.

5. The process of claim 4 provided with the step of contacting said dry gas stream with a solvent absorbent and removing $CO_2$ therefrom.

6. The process of claim 1 wherein the weight ratio U/Ni in the catalyst in (1) is in the range of about 7-1, and at least 30 to about 80 weight percent of the nickel in the catalyst is in the metallic state.

7. The process of claim 1 where in step (1) said nickel uranate is at least one member selected from the group consisting of $NiUO_4$ and $NiU_3O_{10}$, and said oxide of nickel is at least one member selected from the group consisting of NiO and $Ni_3O_4$.

8. The process of claim 1 where in step (1) said alkali-metal promotor is at least one member selected from the group consisting of potassium, sodium, and cesium.

9. The process of claim 1 wherein the uranium in the catalyst composition in (1) comprises at least 99.7 weight percent $^{238}U$ isotope.

10. A process for the production of a methane-containing gas comprising:

(1) reacting a hydrocarbonaceous material by partial oxidation with a free-oxygen containing gas optionally in the presence of a temperature moderator at an autogenous temperature in the range of about 1700° to 3000° F. and a pressure in the range of about 1 to 300 atmospheres in the reaction zone of a free-flow unpacked non catalytic synthesis gas generator to produce an effluent gas stream comprising $H_2$, CO, $H_2O$, and at least one member selected from the group consisting of $CO_2$, $CH_4$, COS, $H_2S$, Ar, $N_2$, particulate carbon, and ash;

(2) cooling, cleaning and optionally purifying at least a portion of the gas stream from (1) to obtain a feed gas stream comprising carbon monoxide and $H_2$ and/or $H_2O$ and at least one member selected from the group consisting of $CH_4$, $CO_2$, $N_2$, and Ar;

(3) introducing the cooled, cleaned and purified feed gas stream from (2) into a reaction zone containing an unsupported catalyst consisting of an alkali-metal promoted partially reduced mixture of at least one nickel uranate selected from the group consisting of $NiUO_4$ and $NiU_3O_{10}$ and at least one oxide of nickel selected from the group consisting of NiO and $Ni_3O_4$; and wherein the total weight of uranium present in the catalyst in (3) based on the total weight of said catalyst composition is in the range of over 50 to about 90 weight percent, the weight ratio U/Ni in the catalyst in (3) is in the range of about 5-2, and at least 30 to about 80 weight percent of the nickel in the catalyst in (3) is in the metallic state; and reacting said feed gas stream at a temperature in the range of about 375° to 1500° F. and at a pressure in the range of about 1 to 300 atmospheres; and (4) removing a methane-containing product gas stream from said reaction zone in (3).

11. The process of claim 10 wherein the mole ratio of either $H_2/CO$ or $H_2O/CO$ in the feed gas mixture reacted in (3) is in the range of 0 to about 5 and the other mole ratio is in the range of about 0.3 to 5.

12. The process of claim 10 wherein the uranium in the catalyst composition in step (3) comprises at least 99.7 wt. % $^{238}U$ isotope.

13. The process of claim 10 wherein the feed gas stream from (2) is introduced into a fixed bed of catalyst in step (3) at a space velocity in the range of 350–10,000 vol./vol./hr..

14. The process of claim 10 wherein the alkali-metal promoter in step (3) is at least one member selected from the group consisting of potassium, sodium, and cesium.

15. The process of claim 10 wherein the catalyst composition in step (3) before partial reduction comprises a mixture of the following materials in weight percent: NiO 1.0 to 30, $Ni_3O_4$ trace to 30, $NiUO_4$ 70 to 98, and $K_2O$ 0.01 to 2.0.

16. The process of claim 10 wherein the catalyst composition in step (3) before partial reduction comprises a mixture of the following materials in weight percent: NiO 1.0 to 30, $NiU_3O_{10}$ 70 to 98, and $K_2O$ 0.01 to 2.0.

17. The process of claim 10 wherein the catalyst composition in step (3) before partial reduction comprises a mixture of the following materials in weight percent: NiO 1.0 to 30, $NiUO_4$ 30 to 68, and $NiU_3O_{10}$ 30 to 68, and $K_2O$ 0.01 to 2.0.

18. The process of claim 10 wherein the pressure in steps (2) through (4) is substantially the same as the pressure in the gas generator in step (1) less ordinary drop in the lines.

19. The process of claim 10 provided with the step of cooling the gas stream from (4) by indirect heat exchange with the purified feed gas stream from (2).

20. The process of claim 10 provided with the added step of cooling all or a portion of the gas stream from (4) below the dew point and condensing out and separating $H_2O$ from said gas stream to produce a $CH_4$-rich gas stream comprising at least 25 volume percent $CH_4$.

21. The process of claim 20 wherein 1–25 volumes of said dewatered gas per volume of fresh feed gas from step (2) are recycled through the catalytic reaction zone in step (3).

22. The process of claim 20 provided with the added step of removing $CO_2$ from the dewatered $CH_4$-rich gas stream.

23. The process of claim 22 with the added step of recycling the $CO_2$ separated from the process gas stream to the partial oxidation gas generator in (1) as at least a portion of the temperature moderator.

24. The process of claim 10 wherein said hydrocarbonaceous feed is selected from the group consisting of petroleum distillate and residua, gas oil, residual fuel, reduced crude, whole crude, asphalt, coal tar, coal derived oil, shale oil, tar sand oil, and mixtures thereof.

25. The process of claim 10 wherein said hydrocarbonaceous feed is a pumpable slurry of solid carbonaceous feed selected from the group consisting of coal, lignite, coal char, particulate carbon, petroleum coke, and mixtures thereof in $H_2O$ or in a liquid hydrocarbonaceous fuel.

26. The process of claim 10 wherein said hydrocarbonaceous feed is a liquid hydrocarbon material containing combined oxygen selected from the group consisting of alcohols, ketones, aldehydes, organic acids, esters, ethers, and mixtures thereof, optionally in admixture with a liquid petroleum material.

27. The process of claim 10 wherein said free-oxygen containing gas is selected from the group consisting of air, oxygen-enriched air (22 mole percent $O_2$ and higher), and preferably substantially pure oxygen (95 mole percent $O_2$ and higher.

28. The process of claim 10 wherein the catalyst in step (3) is promoted with about 0.01 to 2.0 weight percent of an oxide of said alkali-metal.

29. The process of claim 10 wherein the unpurified portion of said cooled and cleaned gas stream from step (2) is mixed with the purified portion and the mixture is introduced into the reaction zone in step (3) with or without admixture with recycle gas.

* * * * *